(12) United States Patent
Zehtab et al.

(10) Patent No.: US 9,480,506 B2
(45) Date of Patent: Nov. 1, 2016

(54) COMPRESSION DEVICE FOR INTERLOCKING COMPRESSION NAILING SYSTEMS AND METHOD OF USE

(71) Applicants: Mohammad Javad Zehtab, Tehran (IR); Mojtaba Lotfaliany Abrand Abadi, Tehran (IR); Morteza Nazari Nodoushan, Tehran (IR)

(72) Inventors: Mohammad Javad Zehtab, Tehran (IR); Mojtaba Lotfaliany Abrand Abadi, Tehran (IR); Morteza Nazari Nodoushan, Tehran (IR)

( * ) Notice: Subject to any disclaimer, the term of this patent is extended or adjusted under 35 U.S.C. 154(b) by 0 days.

(21) Appl. No.: 14/594,153

(22) Filed: Jan. 11, 2015

(65) Prior Publication Data

US 2016/0199109 A1    Jul. 14, 2016

(51) Int. Cl.
*A61B 17/58* (2006.01)
*A61B 17/72* (2006.01)

(52) U.S. Cl.
CPC .................... *A61B 17/7233* (2013.01)

(58) Field of Classification Search
CPC .. A61B 17/72; A61B 17/216; A61B 17/225; A61B 17/744; A61B 17/7233; A61B 17/7241; A61B 17/725
See application file for complete search history.

(56) References Cited

U.S. PATENT DOCUMENTS

| | | | | |
|---|---|---|---|---|
| 5,176,681 A * | 1/1993 | Lawes | ................. | A61B 17/921 606/64 |
| 5,505,734 A * | 4/1996 | Caniggia | ............ | A61B 17/7225 606/63 |
| 6,228,086 B1 * | 5/2001 | Wahl | .................. | A61B 17/7225 606/62 |
| 6,921,400 B2 * | 7/2005 | Sohngen | ................ | A61B 17/68 606/62 |
| 7,601,153 B2 * | 10/2009 | Shinjo | .................. | A61B 17/744 606/62 |
| 8,562,606 B2 * | 10/2013 | Richter | ............. | A61B 17/1682 606/62 |
| 8,915,917 B2 * | 12/2014 | Doherty | ............. | A61B 17/7225 606/62 |
| 2004/0260290 A1 * | 12/2004 | Zander | ................... | A61B 17/72 606/67 |
| 2006/0173457 A1 * | 8/2006 | Tornier | .................. | A61B 17/72 606/62 |
| 2008/0183171 A1 * | 7/2008 | Elghazaly | ............ | A61B 17/744 606/64 |
| 2008/0294164 A1 * | 11/2008 | Frank | ................. | A61B 17/7241 606/64 |
| 2010/0249781 A1 * | 9/2010 | Haidukewych | .... | A61B 17/7241 606/62 |
| 2012/0197255 A1 * | 8/2012 | Elghazaly | ............ | A61B 17/725 606/64 |

* cited by examiner

*Primary Examiner* — Mary Hoffman
(74) *Attorney, Agent, or Firm* — Barry Choobin; Patent 360

(57) ABSTRACT

A compression device and method for interlocking compression nailing systems provide a compression force onto fracture site and a bone fixed between proximal and distal parts of intramedullary nail to prevent stress shielding and improve healing. The compression device having pre-assembled components of set screw, elastic component, distal cap and connector screw are rotated. After nail insertion, the nail is fixed to the bone fragments by inserting the fasteners into distal bores and proximal slot. The compression device is inserted within the bore of the nail. The set screw is screwed to move elastic component and distal cap to push the proximal bone fragment distally. Distal cap overlies on fastener screw shaft to spread compression forces in fastener screw surface to prevent stress concentration. After fracture gap minimization, the set screw is screwed further to compress elastic component to provide desired compression force.

9 Claims, 7 Drawing Sheets

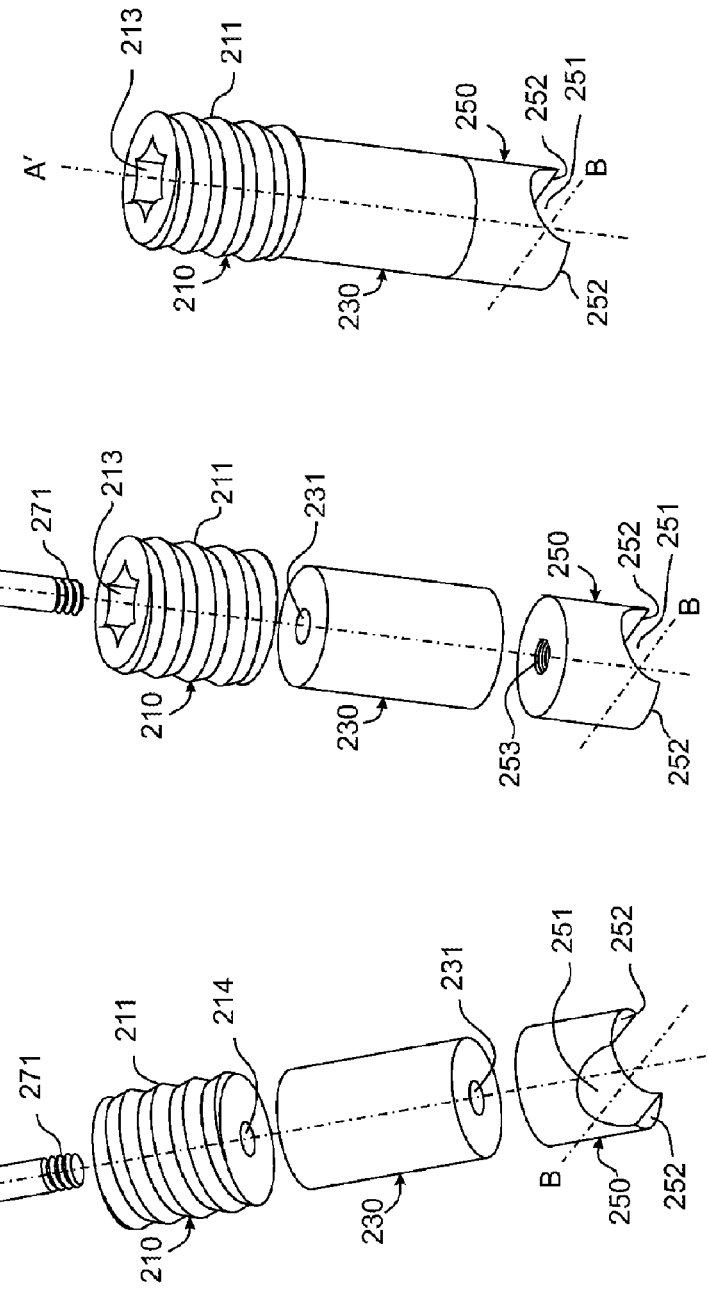

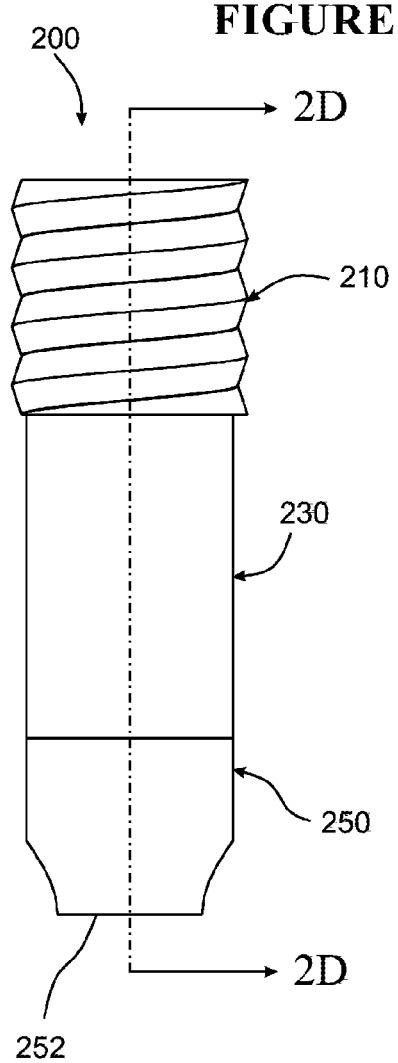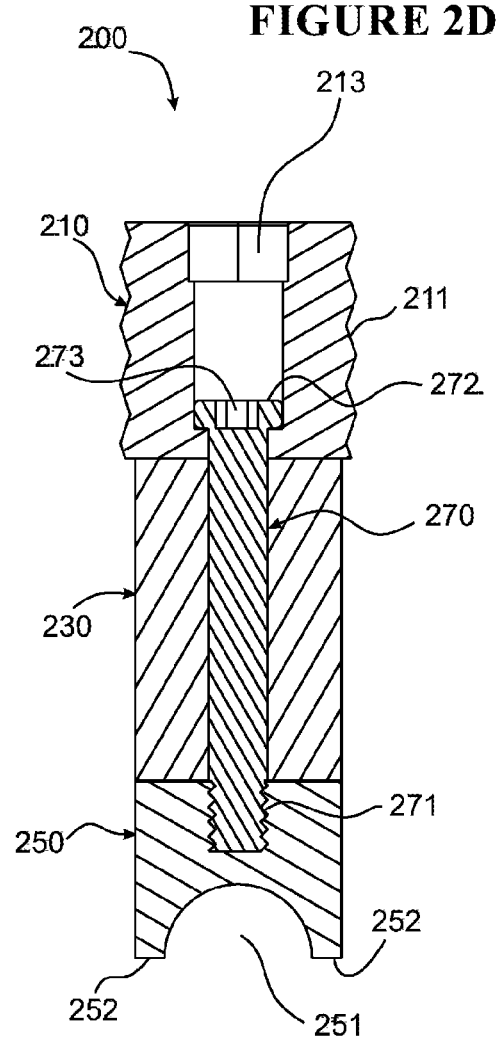

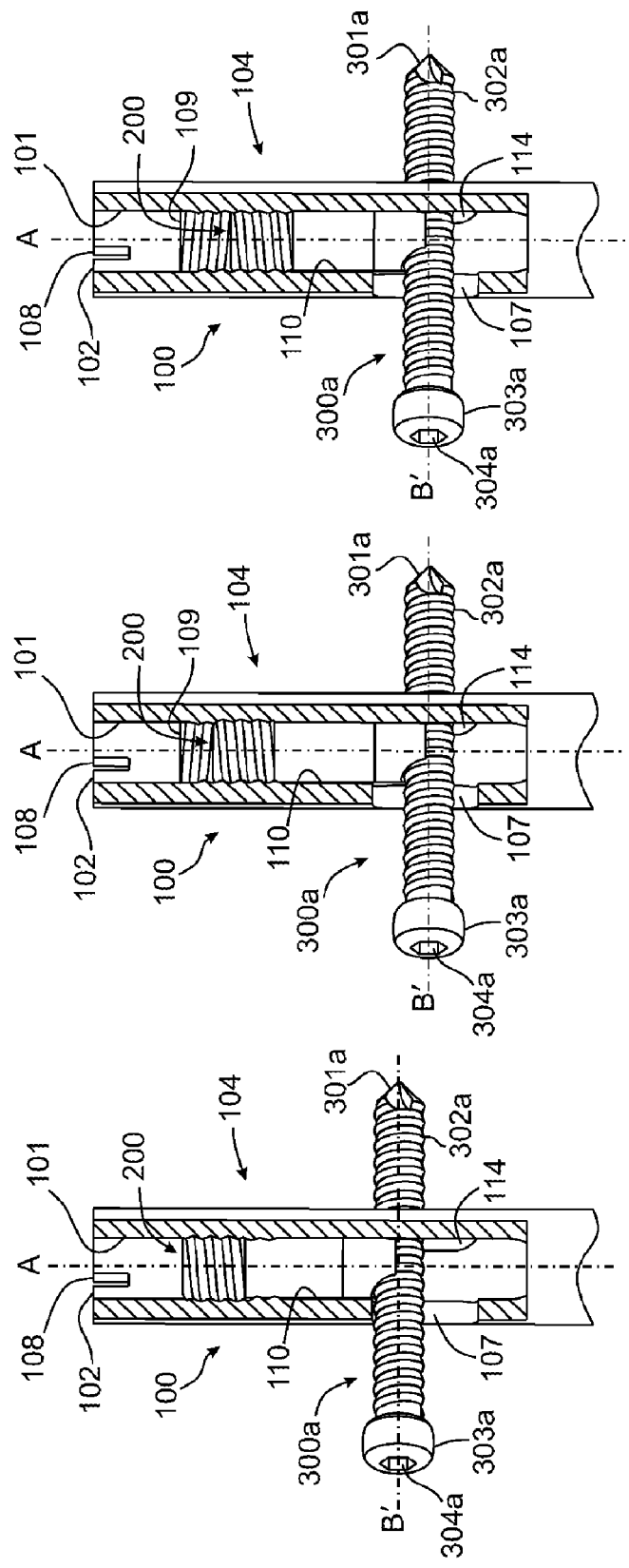

COMPRESSION DEVICE FOR INTERLOCKING COMPRESSION NAILING SYSTEMS AND METHOD OF USE

SPONSORSHIP STATEMENT

The present invention is sponsored by Tehran University of Medical Sciences (TUMS) for international filing.

THE FIELD OF INVENTION

The present invention relates to a compression device as an add-on for interlocking compression nailing systems which are well known for treating a range of long bone disorders.

BACKGROUND OF THE INVENTION

For the first time, a reliable and successful method of intramedullary nailing was introduced by Kuntscher. To avoid axial and rotational instability, new generations of intramedullary nailing systems were interlocked proximally and distally. Nowadays the interlocking nailing is the method of choice for treating a range of long bone disorders used by trauma and orthopedic surgeons world widely. This method offers a device with excellent stability against the axial and rotational deformation, involves much less surgical exposure and reduces the risk of infection; however, it fails to exert a compression onto the fracture site and fixed bone fragments.

The important role of compression force in normal bone remodeling and bone healing is well known. The absence of adequate weight bearing forces onto bone tissue, such as what happened in bone fixation with an intramedullary nail may lead to inhibition of osteogenesis in fracture site and whole fixed bone fragments (stress shielding effect). Stress shielding effect can results in an increase in osteoporosis rate, fatigue fracture, mal- and non-union susceptibility (1, 2) (3) (4)

Present disclosure introduces the "compression device" as an add-on for interlocking compression nailing systems provides an active inherent compression onto fracture site and whole bone fixed between proximal and distal part of nail prevents osteoporosis due to stress shielding effect, improve bone healing development and emends deficiencies of interlocking compression nailing and similar devices known in the art.

The special interest in compression nailing started in the late 1960s in an effort to combine the advantages of compression osteosynthesis to the intramedullary nailing. One of the initial compression nails, had a tie rod placed within a Kuntscher nail anchored to the distal fracture fragment by cross pinning. The fracture fragments fixation involves sliding a Kuntscher nail over a tension rod and then fixing the clevis of tension rod to distal bone fragment by a transverse screw. The Kuntscher nail is fixed to proximal bone fragment by a metal lip. After compression achievement, a locking sleeve that is fixed by a screw to the tension rod prevents loss of compression.

Huckstep nail is a four-sided intramedullary compression nail of solid titanium alloy, a mix of 6% aluminum and 4% vanadium. Modulus of elasticity of Huckstep nail material is just about half of conventional nails made of stainless steel or chrome cobalt. Although stress shielding effect is much lower in Huckstep nail in comparison with conventional nails, the stiffness and strength of this nail is noticeably lower than former ones (5).

Telescopic locking nails such as U.S. Pat. Nos. 6,569,165 or 7,608,075 were provided with a lower diameter inner nail mounted in a higher diameter outer tube (telescope part) in proximal portion. A penetrating slot in inner nail and a penetrating hole in outer tube were provided. The proximal locking fastener screws go through both the locking slot of inner nail and the locking hole of telescope part. Consequently, the inner nail can move over a limited distance in the telescope part. After proximal and distal locking, the nail prevents axial and rotational displacement but permits cyclic dynamic compression during weight bearing. Compression also can be applied by means of a compression screw pushes the inner nail in the outer tube (6).

The U.S. Pat. No. 4,875,475 was the first to present an axially inserted compression screw as a simple internal compression device. The device comprises of an intramedullary nail adapted to be driven into a hollow bone and an adjusting means. The proximal portion of nail is provided with an internal threaded portion and a transversely penetrating longitudinal slot penetrates through the nail and will be connected to the bone by a fastener screw. An adjusting means comprises of a bolt as adjusting component provided with an external threaded portion screwed directly into the internal threaded portion of the nail. The bolt is adapted to be brought into direct or indirect engagement with the fastener screw transversely penetrating through the longitudinal slot. By screwing the bolt, the fastener screw will be pressed toward the distal end of the nail.

Although the above mentioned inventions' ideas are valuable enough, none of them are manufactured in series nowadays due to various biomechanical or application obstacles. The interlocking compression nailing systems which were introduced as a new generation of nailing systems provide the option of compression achieved by an internal mechanism. Although a wide range of interlocking compression nailing systems were designed and manufactured such as U.S. Pat. Nos. 7,771,428, 7,867,231 and 7,942,876 with regards to different indications and economic considerations, the method of compression exertion were preserved in almost all of them (7-9). Generally, an interlocking compression nailing system consists of a cylindrical intramedullary nail adapted to be driven into a hollow bone comprising a longitudinal hole. Proximal portion of nail is provided with internal threads and a penetrating longitudinal slot. The distal portion of nail is provided with two transverse penetrating circular bores. A compression force onto fracture site can be achieved by using two different methods of dynamic and contact compression. In dynamic method, after nail insertion in reamed cavity of fractured bone, the intramedullary nail is fixed to bone fragments by two fastener screws inserted in distal bores and a fastener screw inserted in proximal end of longitudinal slot. In this way, the proximal bone fragment can freely move along longitudinal axis of nail in the whole length of longitudinal slot while it is immobilized in rotational and axial movements due to inter-locking. Hence, bone fragments are subjected to weight bearing forces of relevant body parts; however, in this method, fracture site instability and bone healing disturbance can be occurred due to moveable fixation of proximal bone fragment to the intramedullary nail. Furthermore, in the unloaded state, weight of the extremity will cause tensile stresses in fracture site that may pushes the bone fragments apart. To prevent macro-movements in fracture site, in contact method, a compression screw which is screwed to the internal threaded portion of longitudinal hole pushes the proximal fastener screw toward fracture site and approximates bone fragments to each other. In this way, movement range of proximal bone fragment was restricted and macro-movements were prevented; however, even contact method did not also provide the ideal and perfect answer to stress shielding avoidance. It should be kept in mind that interlocking compression nailing systems rely on muscular and weight bearing forces to exert the compression force, without any inherent compression force of device itself. Consequently their privileges diminished in patients treated by non-weight-bearing or postponed-weight-bearing protocols. In addition, frequently presence and absence of compression in fracture site during weight bearing may be painful for patients and also may distract the fracture site (10).

A suggested way to provide an active compression in interlocking compression nailing systems is putting force to bend the shaft of proximal fastener screw. In this way, although a bended fastener screw can provide an active compression, there are some disadvantages. First of all, there is a relatively high risk of fastener screw failure by forcing it to bend. Second, although the materials are used in fastener screws have significantly satisfactory stiffness and strength; they do not have sufficient elasticity needed to impose adequate bending force. Thus merely bending of fastener screw may not provide a sufficient compression force onto fracture site. Third, there is not a reliable measurement method to evaluate the compression force exerted onto fastener screw and fracture site that may lead to screw failure due to over tightening or insufficient compression onto fracture site due to inadequate tightening. In addition, it should be taken into account that a wide range of compression forces onto fracture site may lead to a significant difference in patients' outcomes.

Interlocking compression nailing, beyond of its failure to prevent stress shielding effect, was momentous achievement in the field of traumatology and orthopedic and reached a remarkable improvement in patients' outcome because of significant advantages of device in a broad spectrum of indications such as long bone fractures, pseudarthroses, malalignment, arthrodesis, post traumatic problems and reconstructive orthopedic surgeries. Briefly, the main privileges of interlocking compression nailing method in comparison with other alternatives are post-operative early weight-bearing, easy application, more stability, less surgical exposure and a significant reduction in infection risk (11-14) (.

Finally, although some inventions such as the dynamic compression nail described a modified nail designed to achieve axial compression onto fracture site using self-compression locking screws, interlocking compression nailing system seems irreplaceable method due to a broad spectrum of privileges in comparison with other alternative methods (15, 16).

SUMMARY OF THE INVENTION

The object of this invention is to introduce the "compression device" as an add-on for interlocking compression nailing systems which provides an active inherent compression force onto fracture site and whole bone fixed between proximal and distal part of nail to prevent stress shielding effect, improve bone healing development and emend deficiencies of interlocking compression nailing and similar devices known in the art. A further object of the invention is to create a compression device which is simple in design, inexpensive in manufacture, flexible in use, compatible with almost all of conventional interlocking compression nails, biocompatible enough to remain within implant for long terms and does not impose any additional invasive procedure on patients.

The compression device is composed of four pre-assembled components as following: set screw, elastic component, distal cap and connector screw. These components are pre-assembled longitudinally by connector screw. Set screw is a cylindrical headless screw threaded in the whole of its length with female threads adapted to be brought into direct engagement with internal threads of nail longitudinal bore. In addition, set screw has a penetrating longitudinal bore restricted in distal opening by a surrounding flange limits the outlet diameter. Elastic component is a cylindrical segment with a longitudinal bore. Elastic component is made of polycaprolactone, a biocompatible polymer, which has unique elastic properties in compression to provide a satisfactory compression force onto fracture site and bone fragments in reasonable length changes and it also has adequate strength and hardness to withstand physiologic compression forces. Moreover, this material is biocompatible enough to apply in long term implants. Distal cap is a cylindrical segment provided with a distal semicircular opening extended transversely and defined between two diametrically opposed end extensions. The distal opening is adapted to be brought into direct engagement with fastener screw shaft. In addition, distal cap was provided with an internally threaded hole in proximal surface to receive connector screw. Connector screw is a thin screw passes through the set screw and elastic component longitudinal bores and is screwed tightly to distal cap hole. In this way, connector screw connects compression components longitudinally while they are free for rotation.

The compression device is inserted into the nail longitudinal bore by means of a screw driver. By screwing the set screw in the proximal threaded portion of nail, elastic component and distal cap move through longitudinal bore until the shaft of proximal fastener screw come into engagement with the distal opening of compression device. Screwing the set screw deeper into the nail longitudinal bore moves the proximal fastener screw along the longitudinal slot from proximal end toward distal end of longitudinal slot. Due to tight fixation between proximal bone fragment and proximal fastener screw, the proximal bone fragment moves along longitudinal axis with fastener screw until the fracture gap is minimized.

After gap minimization, further screwing of set screw merely compresses the elastic component longitudinally with regards to its elastic properties. In this way, compressed elastic component supplies an active reliable permanent compression onto fracture site and both bone fragments through providing desired force onto the shaft of proximal fastener screw.

BRIEF DESCRIPTION OF THE SEVERAL VIEWS OF THE DRAWING

FIG. 2 is a perspective view of a pre-assembled compression device.

FIGS. 2A and 2B are perspective views of an exploded compression device.

FIG. 2C is an elevated side view of the compression device of FIGS. 2A and 2B.

FIG. 2D is a sectional view of the compression device of FIG. 2C taken along line 2D-2D.

FIGS. 3-3B are various perspective views of the first, second and third position of compression device in the intramedullary nail longitudinal bore during insertion. The nail is partially broken away.

DETAILED DESCRIPTION OF THE INVENTION

The following description is merely serving as an example and there is not any intention to limit the invention, its application. The present invention can be used for treating a broad spectrum of diseases and disorders such as other hollow bones fractures, pseudarthroses, malalignment, arthrodesis, post traumatic problems and reconstructive orthopedic surgeries. General surgical procedures are outlined only as needed to demonstrate the devices and methods provided by the present description while details of standard and known procedures and instruments are omitted for simplicity and brevity.

Figure 1:
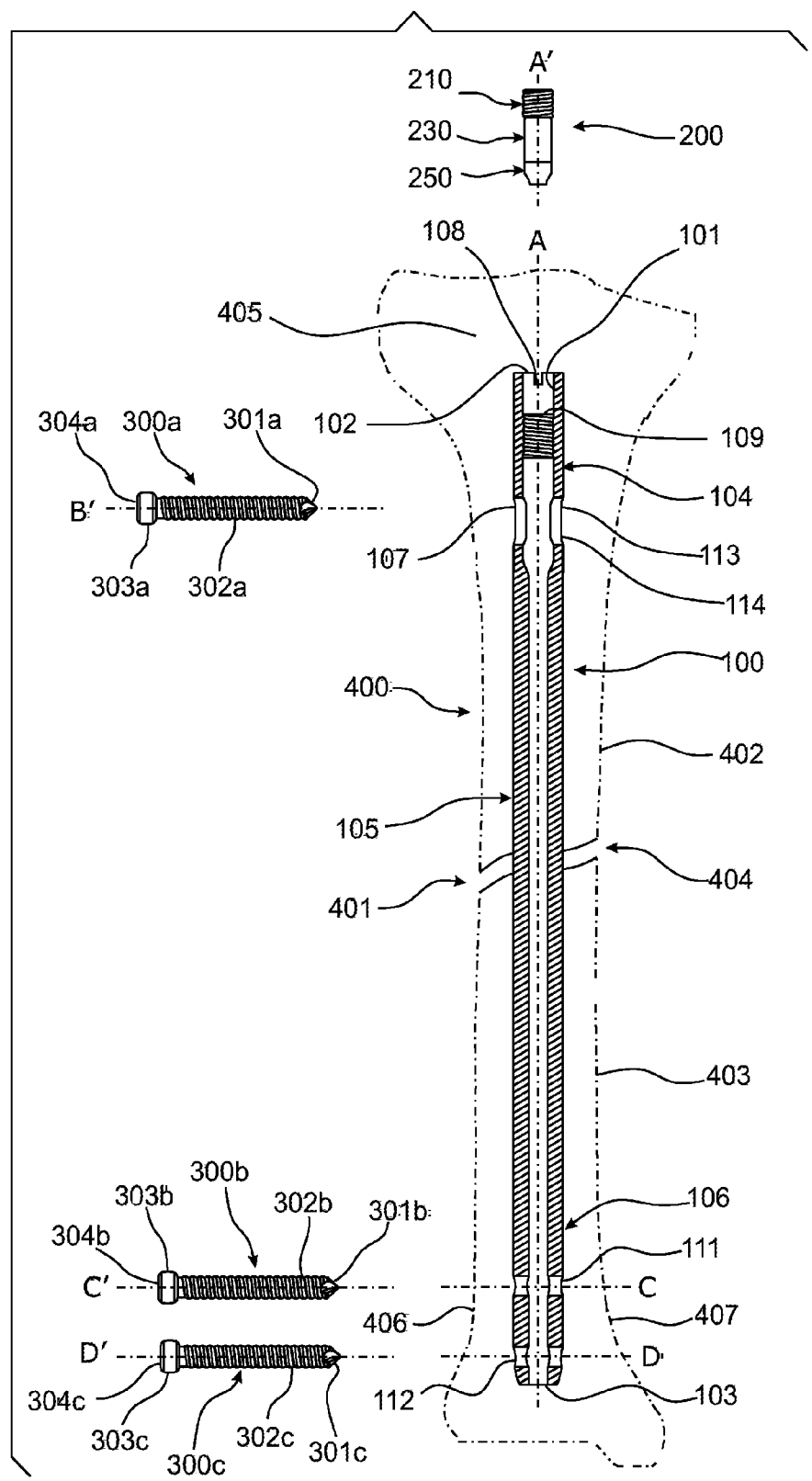
FIG. 1 shows an environmental view of an exploded exemplary interlocking compression nailing system implanted for a fixation of a transverse fracture in shaft of tibia. The intramedullary nail is shown in section and outline of bone is illustrated by dash-dotted lines.

Referring to FIG. 1, an exemplary interlocking compression nailing system comprises an intramedullary nail 100, a compression device 200 and three fastener screws 300a, 300b, 300c as its main components. Furthermore, the outline of fractured bone 400 is shown in FIG. 1 by dash-dotted lines. The bone 400 is fractured in the location of fracture site 401 into two bone fragments 402, 403, whereas a fracture gap 404 segregates two bone fragments from each other.

Figure 1A:
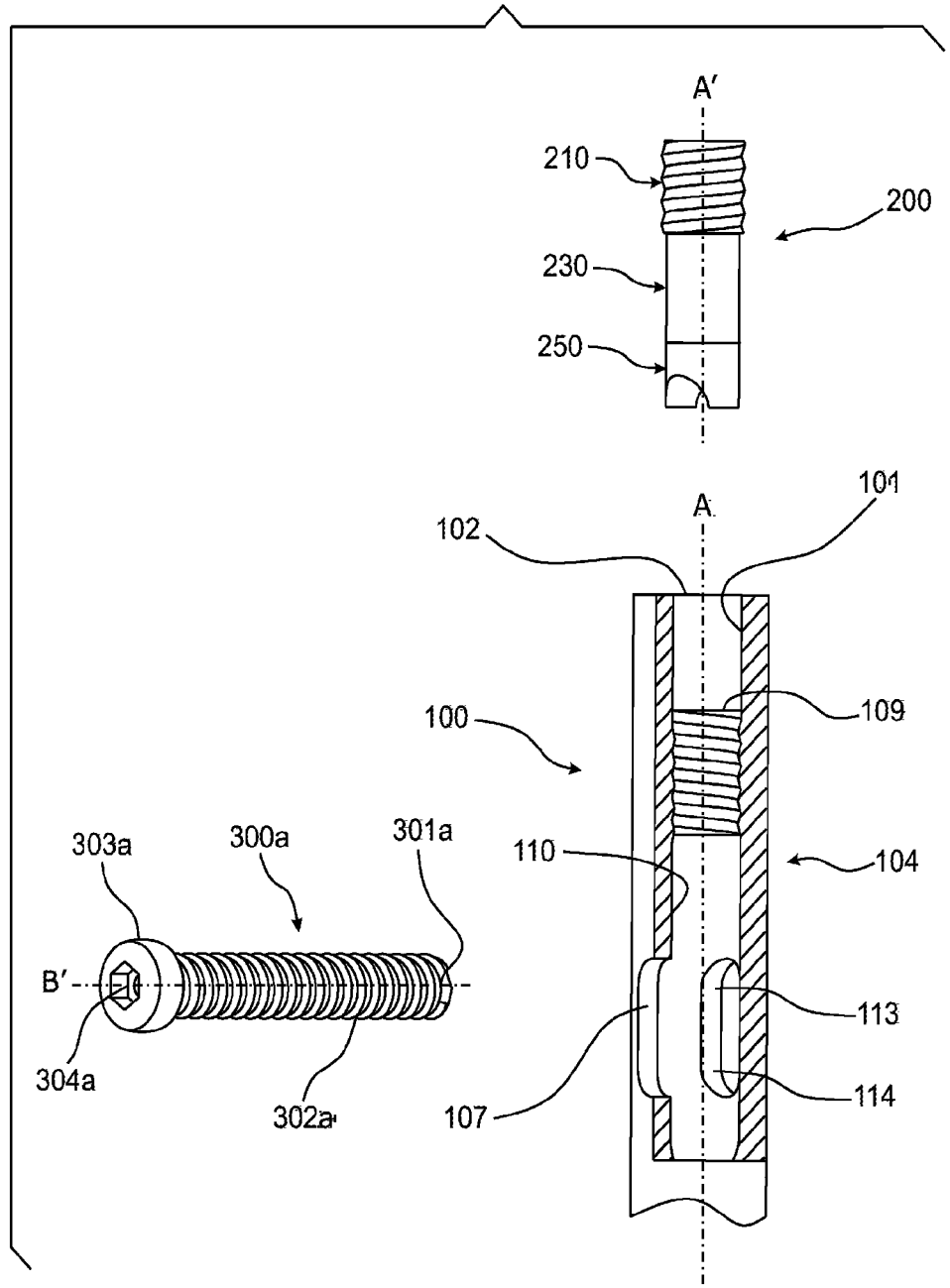
FIG. 1A is a perspective view of the proximal end of an exploded intramedullary nail. The nail is partially broken away.

Referring to FIG. 1 and FIG. 1A, intramedullary nail 100 is a one-fragment longitudinal cylindrical nail comprising a penetrating longitudinal bore 101 runs along with longitudinal axis A and opens at both free ends of the nail 102, 103. The intramedullary nail 100 is designed into three portions: proximal portion 104, middle portion 105, and distal portion 106. Proximal portion 104 is provided with a penetrating longitudinal slot 107 expanded in parallel to the longitudinal axis and A penetrates transversely through the nail 100. In free end of proximal portion 102, two diametrically opposed recesses 108 are provided to be brought into engagement with mating protrusions of an insertion/extraction instrument (not shown). Moreover, proximal portion of nail 104 is provided with an internal threaded portion 109 with male threads. A non-threaded portion 110 separates the threaded portion 109 from longitudinal slot 107 to prevent gripping and disturbance in proximal fastener screw 300a insertion in longitudinal slot 107. The distal portion of nail 106 is provided with two transverse penetrating circular bores 111, 112 transversely penetrate to the nail 100 and cross the longitudinal bore along transverse axes C and D, which are perpendicular to the longitudinal axis A. Each fastener screw 300a, 300b, 300c contains a self-cutting threaded nib 301a, 301b, 301c, a threaded shaft 302a, 302b, 302c and a head 303a, 303b, 303c has a countersunk surface 304a, 304b, 304c for a screw driver.

Figure 2E:
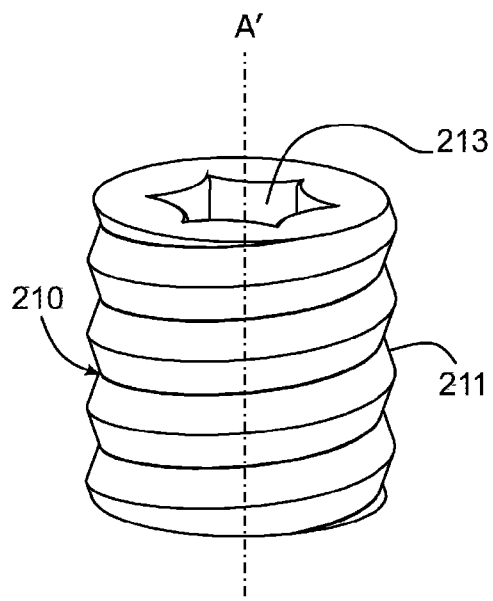
FIGS. 2E and 2F are perspective views of the set screw of compression device.
Figure 2F:
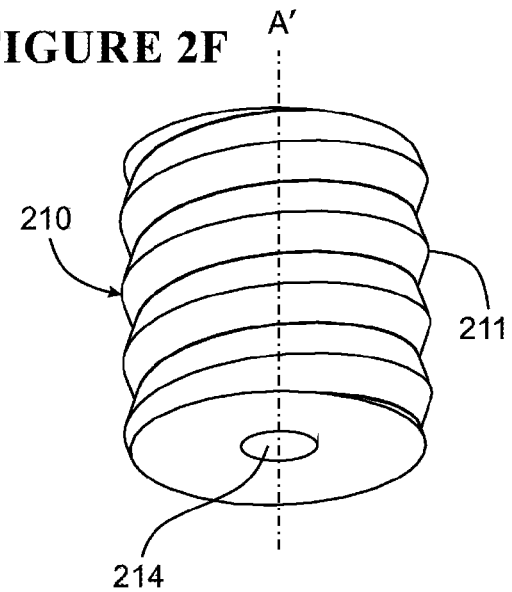
Figure 2G:
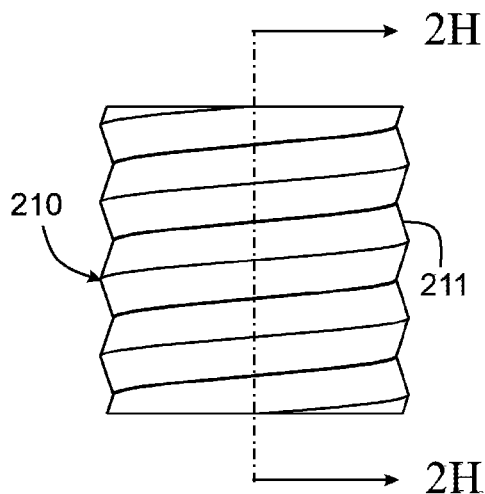
FIG. 2G is an elevated side view of the set screw of FIGS. 2E and 2F.
Figure 2H:
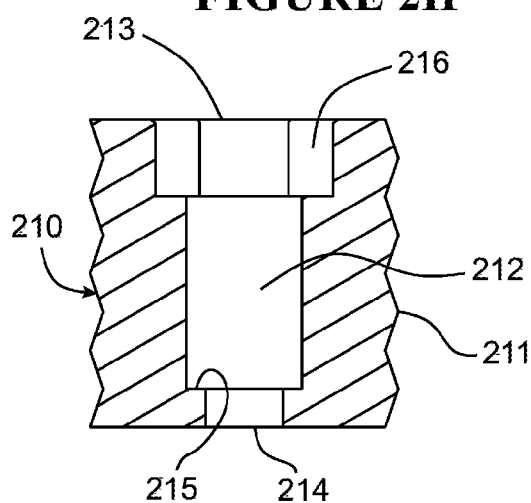
FIG. 2H is a sectional view of the set screw of FIGS. 2G taken along line 2H-2H.
Figure 2I:
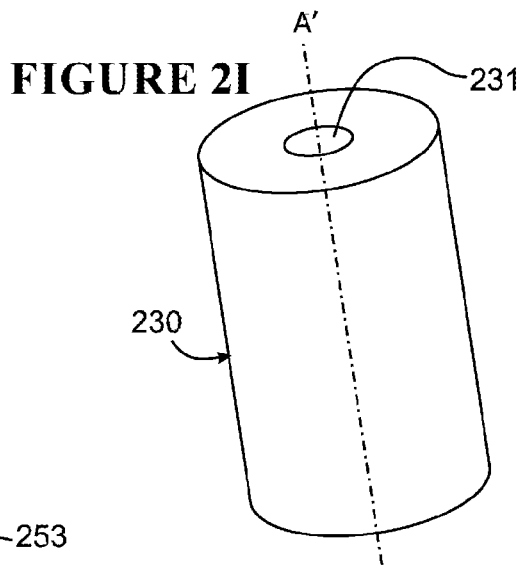
FIG. 2I is perspective view of the elastic component of compression device.
Figure 2J:
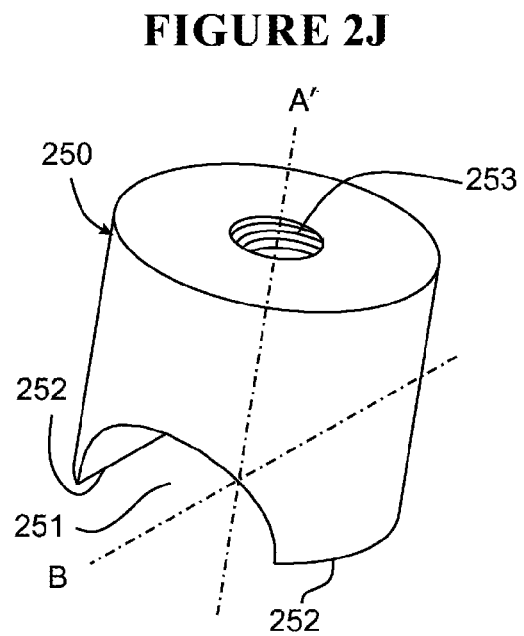
FIG. 2J is perspective view of the end cap of compression device.
Figure 2K:
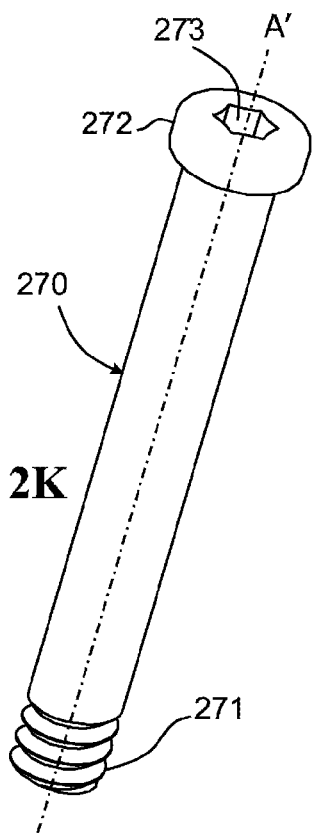
FIG. 2K is perspective view of the connector screw of compression device.

Referring FIGS. 2-2K, compression device 200 includes four pre-assembled components as following: set screw 210, elastic component 230, distal cap 250, and connector screw 270. These components are pre-assembled together along longitudinal axis A' of compression device 200 by connector screw 270. Set screw 210 is a cylindrical headless screw threaded in the whole of its length with female threads 211 adapted to be brought into direct engagement with internal threads of nail longitudinal bore 101. In addition, set screw 210 has a penetrating longitudinal bore 212 runs along with longitudinal axis A' and opens at both free ends of the set screw 213, 214. Distal opening of set screw longitudinal bore 214 is restricted by a surrounding flange 215 limits the outlet diameter. Set screw 210 also is provided with a driver engagement formation 216 in proximal surface.

Elastic component 230 is a cylindrical segment with a longitudinal bore 231 runs along axis A' and opens at both free ends. Elastic component is made of a biocompatible polymer has adequate strength and hardness to withstand physiologic forces and in addition is elastic enough to provide a satisfactory compression force onto fracture site 401 and bone fragments 402, 403 with reasonable length changes. Moreover, this material is biocompatible enough to apply in long term implants.

Distal cap 250 is a cylindrical segment provided with a distal semicircular opening 251 extended transversely along axis B and defined between two diametrically opposed end extensions 252 of distal cap 250. Distal opening is adapted to be brought into direct engagement with it. In addition, distal cap 250 was provided with an internally threaded hole 253 in proximal surface to receive distal part of connector screw 271.

Connector screw 270 is a thin screw pass through the set screw and elastic component longitudinal bores 212, 231 and screwed tightly to distal cap hole 253. Connector screw is brought to engagement with distal cap hole threads with its threaded portion 271 located in its distal part. In this way, connector screw connects compression components tightly in longitudinal axis A' while they are free in rotational from each other around longitudinal axis A'. Moreover, connector screw head 272 is provided with a screw driver engagement formation 273.

The optimal material with acceptable properties for using in elastic component is polycaprolactone, a hydrophobic semi-crystalline polymer having a glass transition temperature of −60° C. and melting point ranging between 59 and 64° C. Due to low glass transition temperature, polycaprolactone is in a rubbery state at physiological and room temperature provides exclusive mechanical properties in tensile and compression (17-19). Furthermore, polycaprolactone has been known as a degradable biocompatible polymer; however, it degrades much slower(up to 3 years) than other degradable biopolymers such as polyglycolide, poly d,l-lactide and its copolymers (20-22). A large number of in vitro and in vivo investigations have shown the safety and biocompatibility of this material in short and long term implants (23-26). Unique elastic properties and inexpensive production provide a promising platform for the design and fabrication of long term implants such as compression device (27-32). Moreover, the material strength, stiffness and crack resistance can improve by increasing molecular weight or blending with other biocompatible polymers.

EXAMPLE 1

Standard techniques of intramedullary nailing can be used for compression device application as it is briefly explained in coming sections. For simplicity and repetition avoidance, surgery procedures were not illustrated in drawings in step by step manner. Outlined were described only as needed to demonstrate the devices and methods while details of standard and known procedures and instruments are omitted.

First, a standard midline patella tendon splitting approach is used for the affected limb. Second, the entry point is obtained using an awl (not shown). Then, reduction is achieved manually in order to bone fragments 402, 403 be aligned to each other. After that, a ball-tipped guide-wire (not shown) is inserted across the fracture site 401 to the distal bone fragment 403. Next, reaming is done over the guide-wire (not shown) slightly beyond the nail diameter. In this point, an intramedullary nail with appropriate length and diameter is selected. The nail 100 used for compression nailing should have appropriate size and strength and also can slide freely in the medullar cavity (not shown). An insertion/exertion instrument (not shown) temporarily is fastened to the nail proximal end 102 by means of a fixing screw (not shown) and proximal opening recesses 108. Then, the nail 100 is inserted over a smooth guide-wire (not shown) into the hollowed medullary cavity (not shown) starting out from the bone proximal end and reaches the point shown in FIG. 1. In this point, the nail proximal portion 104 is located in the bone proximal metaphysis and the nail distal portion 106 is located in the distal metaphysis. To fix the nail 100 centrally and avoid rotational and axial instability, the nail 100 is interlocked proximally and distally with self-tapping fastener screws 300a, 300b, 300c. The position of the distal nail bores 111, 112 and proximal nail slot 107 will be determined by means of a targeting device (not shown). When screw holes of targeting device are aligned with the distal nail bores 111, 112, bone will be drilled along with axes C and D. Then distal fastener screws 300b, 300c will be screwed into the drilled holes (not shown), penetrating to nail bores 111, 112 and fix distal bone fragment 403 to the nail 100 in an essentially non-displaceable manner. After fixing distal bone fragment 403 to intramedullary nail 100 tightly, a screw hole (not shown) is drilled into the proximal bone fragment 402 made to align with a portion of the longitudinal slot 107 by preference with a portion located near the proximal end of longitudinal slot 113. Then proximal fastener screw 300a is inserted into the drilled hole and screwed into the bone 400, penetrating to nail longitudinal slot 107 transversely and tightly fixed to near and far bone segments. Consequently, the proximal bone fragment 402 and the nail 100 can freely move relative to each other along longitudinal axis A in the whole length of longitudinal slot 107 while the proximal bone fragment 402 is immobilized in rotational and axial movements. After removing insertion instrument (not shown), compression device 200 is used to move bone fragments 402, 403 toward each other and provides a compression force onto fracture site 401. The compression device 200 is inserted into the nail longitudinal bore 101 by means of a screw driver (not shown). When the compression device 200 is received within the nail longitudinal bore 101, axis A' aligns with the corresponding axis A of the nail 100.

Referring FIG. 3, by screwing the set screw 210 in the proximal threaded portion of nail 109, elastic component and distal cap 230, 250 move along axis A through longitudinal bore 101 until distal opening of distal cap 251 overlies on fastener screw shaft 302a. In this way, the shaft of proximal fastener screw 302a is retained between two end extensions of distal cap 252 and comes into engagement with the distal opening of compression device 251. This engagement is necessary to spread compression forces in fastener screw surface proportionally and also to prevent stress concentration on elastic component 230 and fastener screw shaft 302a.

Referring FIG. 3A, screwing the set screw 210 deeper into the nail longitudinal bore 101 moves the proximal fastener screw 300a along the longitudinal slot 107 from proximal end 113 toward distal end 114 of it. Hence, the proximal bone fragment 402 moves along longitudinal axis with fastener screw 300a until the fracture gap 404 will be minimized thanks to tight fixation between proximal bone fragment 402 and proximal fastener screw 300a.

Referring FIG. 3B, after gap minimization, further screwing of the set screw 210 merely compresses the elastic component 230 along longitudinal axis A regards to its' elastic properties. In this way, compressed elastic component 230 acts as a compressed spring and provides desired compression force onto shaft of proximal fastener screw 302a along longitudinal axis A and supplies an active reliable permanent compression onto fracture site 401 and both bone fragments 402, 403. The compression force onto fracture site 401 can be measured easily by evaluating the length change in elastic component 230 or using a torquemeter.

When intended compression is achieved and two bone fragments 402, 403 get pressed against each other at the fracture site 401 by the compression force, screw driver (not shown) was removed and incision is sutured. Optimal compression force may vary in regards to patient characteristics, type and site of fracture and the disorder tended to be treated by compression device 200.

Importantly, after the operation, in all phases of physiological movements, there is an adequate baseline compression onto fracture site 401 and bone fragments 402, 403 exerted by compression device 200. In other words, in unloaded states, an active compression was exerted onto fracture site 401 and bone fragments 402, 403, while in loaded states fracture site 401 and the bone fragments 402, 403 subjected to both weight bearing forces and compression force exerted by compression device 200 in additive manner. Consequently, macro- movements, fracture site disturbance and stress shielding effect are prevented which improve bone healing process, reduce patients' pain and prevent osteoporosis in fixed bone fragments.

At last but not least, in compression overloading, the elastic component is sacrificed to protect fastener screw from failure thanks to lower failure threshold of elastic component than fastener screw. It stands to reason that the strength of polymer would increase by increasing molecular weight or blending with other biocompatible polymers to provide a suitable elastic component for higher rang of compression forces.

Although present invention has been described with reference to particular embodiments, it is essential to be understood that these embodiments are merely illustrative of the principles and applications of the present invention. Therefore numerous modifications may be made to the descriptive embodiments and other arrangements may be devised without departing from spirit and scope of present invention as defined by the appended claims.

What is claimed is:

1. An interlocking compression nailing system comprising:
   an intramedullary nail adapted to be driven into a hollow bone, and wherein the intramedullary nail comprises a longitudinal bore, and wherein the longitudinal bore is open at both free ends of the intramedullary nail, and wherein the intramedullary nail comprises three portions, and wherein the three portions are a proximal portion, middle portion and a distal portion;
   a plurality of fastener screws provided to fix the intramedullary nail to a plurality of bone fragments in a fractured bone to avoid rotational and axial instability, and wherein the intramedullary nail is interlocked proximally and distally by the plurality of fasteners, and wherein the plurality of fasteners are self-tapping fastener screws, and wherein each fastener screw contains a self-cutting threaded nib, a threaded shaft and a head with a countersunk surface for a screw driver and
   a compression device configured to provide a compression force on a fracture site and the plurality of bone fragments that are fixed between proximal and distal portion of intramedullary nail and wherein the compression device comprises four pre-assembled components, and wherein the pre-assembled components are a set screw, an elastic component, a distal cap and a connector screw, and wherein the elastic component is made of a biocompatible material configured to apply a desired compression force on the fracture site, and wherein the biocompatible material is polycaprolactone;
   wherein the set screw is a cylindrical headless screw with female threads, and wherein the female threads are arranged along an entire length of the screw, and wherein the female threads are adapted to be in direct engagement with the internal threaded portion in the longitudinal bore of the intramedullary nail, and wherein the set screw has a longitudinal bore, and wherein the setscrew has openings at both free ends, and wherein a distal opening of the set screw is restricted by a surrounding flange that limits an outlet diameter of the bore in the setscrew.

2. The system according to claim 1, wherein the proximal portion of intramedullary nail is provided with an internal threaded portion and a transversely penetrating longitudinal slot, and wherein the longitudinal slot is expanded in parallel to the longitudinal axis of the intramedullary nail and wherein the distal portion of nail intramedullary is provided with two transverse penetrating circular bores, and wherein the circular bores are configured to transversely penetrate the intramedullary nail and cross the longitudinal bore.

3. The system according to claim 1, wherein the elastic component is a cylindrical component with a longitudinal bore that is open at both free ends.

4. The system according to claim 1, wherein the distal cap is a cylindrical component provided with a semicircular opening at distal end, and wherein the semicircular opening is extended transversely and defined between two diametrically opposed end extensions of the distal cap, and wherein the distal opening is shaped to be in a direct engagement with the shaft of the fastener screw, and wherein the distal cap is provided with an internally threaded hole in a proximal end to receive a distal end of the connector screw.

5. The system according to claim 1, wherein the connector screw is a thin screw with a threaded portion at a distal end, and wherein the threaded portion of the connector screw is adapted to be in a direct engagement with the threaded hole at the distal cap.

6. The system according to claim 1, wherein the connector screw is configured to pass through the longitudinal bores in the set screw and the elastic component and wherein the connector screw is screwed to the hole in the distal cap, and wherein the connector screw is configured to attach the set screw, the elastic component and the distal cap of the compression device longitudinally while the set screw, the elastic component and the distal cap of the compression device are freely rotated around longitudinal axis independently of each other.

7. The system according to claim 1, wherein the compression device is configured to be inserted into the longitudinal bore of the intramedullary nail and screwed into the threaded portion at the proximal end of the intramedullary nail to move the elastic component and the distal cap through the longitudinal bore of the intramedullary nail to overlay the opening at the distal end of the distal cap on the shaft of the fastener screw, to retain the shaft of fastener screw between two end extensions of the distal cap to engage with the distal opening of the compression device.

8. The system according to claim 1, wherein the set screw is configured to be screwed into the longitudinal bore of the intramedullary nail to move the fastener screw along the longitudinal slot to move the bone fragments to minimize a fracture gap.

9. The system according to claim 1, wherein the set screw is configured to be screwed further after minimizing the fracture gap, to compress the elastic component longitudinally to provide a desired compression force on the shaft of fastener screw to enable a permanent compression of the plurality of bone fragments at the fracture site.

* * * * *